US007081482B2

(12) United States Patent
Collier, Jr. et al.

(10) Patent No.: US 7,081,482 B2
(45) Date of Patent: Jul. 25, 2006

(54) USE OF β-ADRENOCEPTOR ANTAGONISTS FOR THE MANUFACTURE OF A MEDICAMENT FOR THE TREATMENT OF DISORDERS OF THE OUTER RETINA

(75) Inventors: Robert J. Collier, Jr., Arlington, TX (US); Louis Desantis, Jr., Fort Worth, TX (US); Michael A. Kapin, Arlington, TX (US)

(73) Assignee: Alcon, Inc., Hunenberg (CH)

( * ) Notice: Subject to any disclaimer, the term of this patent is extended or adjusted under 35 U.S.C. 154(b) by 153 days.

(21) Appl. No.: 10/130,408

(22) PCT Filed: Nov. 29, 2000

(86) PCT No.: PCT/US00/32575

§ 371 (c)(1),
(2), (4) Date: May 15, 2002

(87) PCT Pub. No.: WO01/43737

PCT Pub. Date: Jun. 21, 2001

(65) Prior Publication Data

US 2002/0193373 A1 Dec. 19, 2002

Related U.S. Application Data

(60) Provisional application No. 60/167,993, filed on Nov. 30, 1999.

(51) Int. Cl.
*A61K 31/135* (2006.01)
(52) U.S. Cl. ........................... 514/652; 514/912
(58) Field of Classification Search ................ 514/652, 514/912
See application file for complete search history.

(56) References Cited

U.S. PATENT DOCUMENTS

| 4,252,984 A | 2/1981 | Manoury et al. |
| 4,311,708 A | 1/1982 | Manoury et al. |
| 4,443,432 A | 4/1984 | Garabedian et al. |

FOREIGN PATENT DOCUMENTS

WO  WO 98/10758  3/1998

OTHER PUBLICATIONS

Osborne, et al., "Topically applied betaxolol attenuates NMDA-induced toxicity to ganglion cells and the effects of ischaemia to the retina," Exp. Eye Research, vol. 69:331-342, 1999.
Osborne, et al., "Neuroprotection in Relation to Retinal Ischemia and Relevance to Glaucoma," Survey of Ophthalmology, vol. 43(1):S103-S128, Jun. 1999.
Fabianova, et al., "Centralna serozna chorioretinopatia-liecba betablokatormi," Ceska A Slovenska Oftamologie, vol. 54(6):401-404, Nov. 1998.

Young, Richard, "Solar radiation and age-related macular degeneration," Current Research, vol. 32(4);252-269, Jan.-Feb. 1988.
Noell, et al., "Retinal damage by light in rats," Investigative Ophthalmology, vol. 5(5):450-472, Oct. 1966.
Bressler, et al., "Age-related macular degeneration," Survey Ophthalmology, vol. 32(6):375-413, May-Jun. 1988.
Curico, et al., "Photoreceptor loss in age-related macular degeneration," Investigative Ophthalmology & Visual science, vol. 37(7):1236-1249, Jun. 1996.
Ge-Zhi, et al., "Apoptosis in human retinal degenerations," Transactions of the.American Ophthalmology Society., vol. 94:411-430, 1996.
Abler, et al., "Photic injury triggers apoptosis of photoreceptor cells," Research Communication in Molecular Pathology and Pharmacology, vol. 92(2):177-189, May 1996.
Taylor, et al., "Long-term effects of visable light on the eye," Archives of Ophthalmology, vol. 110:99-104, Jan. 1992.
Naash, et al., "Induced acceleration of photoreceptor degeneration transgenic mice expressing mutant rhodopsin," Investigative Ophthalmology & Visual Science, vol. 37(5): 775-782, Apr. 1996.
LaVail, et al., "Multiple growth factors, cytokines, and neurotrophins rescue photoreceptors from the damaging effects of constant light," Proceedings of the National Academy of Science, vol. 89:11249-11253, Dec. 1992.
Faktorovich, et al., "Photoreceptor degeneration in inherited retinal dystrophy delayed by basic fibroblast growth factor," Nature, vol. 347:83-86, Sep. 1990.
Organisciak, et al., "The protective effect of ascorbate in retinal light damage of rats," Investigative Ophthalmology & Visual Science, vol. 26:1580-1588, Nov. 1985.
Organisciak, et al., "Protection by dimethylthiourea against retinal light damage in rats," Investigative Ophthalmology & Visual Science, vol. 33(5):1599-1609, Apr. 1992.
Lam, et al., "Amekioration of tetinal photic injury in albino rats by dimethylthiourea," Archives of Ophthalmology, vol. 108:1751-1757, Dec. 1990.
Kozaki, et al., "Light-induced retinal damage in pigmented rabbit—2, Effect of alpha-tocopherol," Nippon Ganka Gakkai Zasshi, vol. 98:948-954, Oct. 1998.
Rapp, et al., "Evaluation of retinal susceptibility to light damage in pigmented rats supplemented with beta-carotene," Current Eye Research, vol. 15:219-223; 1995.
Li, et al., "Amelioration of retinal photic injury by a combination of flunarizine and dimethylthiourea," Experience Eye Research, vol. 56:;71-78, 1993.
Edward, et al., "Amelioration of light-induced retinal degeneration by a calcium overload blocker," Archives of Ophthalmology, vol. 109:554-562, Apr. 1991.

(Continued)

*Primary Examiner*—Zohreh Fay
(74) *Attorney, Agent, or Firm*—Teresa J. Schultz; Sally S. Yeager

(57) ABSTRACT

The invention is directed to the use of β-adrenoceptor antagonists for the manufacture of a medicament for the treatment of disorders of the outer retina.

2 Claims, 9 Drawing Sheets

OTHER PUBLICATIONS

Lam, et al., "Methylprednisolone therapy in laser injury of the retina," Graefes Archives of Clinical & Experimental Ophthalmology, vol. 231:729-736, 1993.

Fu, et al., "Dexamethasone ameliorates retinal photic injury in albino rats," Experimental Eye Research, vol. 54:583-594, 1992.

Collier, et al., "Prevention of photic induced retinal injury by eliprodil," Investigative Ophthalmology & Visual Science, vol. 40(4):S159, Mar. 1999.

Li, et al., "Desferrioxamine ameliorates retinal photic injury in albino rats," Current Eye Research, vol. 10(2):133-144, 1991.

Osborne, et al., "In vivo and in vitro experiments show that betaxolol is a retinal neuroprotective agent," Brain Research, vol. 751:113-123, 1997.

Hester, et al., "The direct vascular relaxing action of betaxolol, carteolol and timolol in porcine long posterior ciliary artery," Survey of Ophthalmology, vol. 38:S125-S134, May 1994.

Yu, et al., "Effect of beta blockers and CA2+ entry blockers on ocular vessels," Vascular Risk Factors and Neuroprotection in Glaucoma, (Drance, S. ed.) pp. 123-134, Update, 1996.

Hoste, et al., "The relaxant action of bataxolol on isolated bovine retinal microarteries," Current Eye Research, vol. 13:483-487, 1994.

Bessho, et al., "Vascular effects of betaxolol, a cardioselective B-adrenoceptor antagonist, in isolated rat arteries,"Japan Journal of Pharmacology, vol. 55:351-358, 1991.

Shahinfar, et al., "A pathologic study of photoreceptor cell death in retinal photic injury," Current Eye Research, vol. 10(1):47-59, 1991.

Abler, et al., "Photoic injury triggers apoptosis of photoreceptor cells," Investigative Ophthalmology & Visual Science, vol. 35(4):S1517, Mar. 1994.

Chang, et al., "Apoptotic photoreceptor cell death after traumatic retinal detachment in humans," Archives of Ophthalmology, vol. 113:880-886, Jul. 1995.

Portera-Cailliau, et al., "Apoptotic photoreceptor cell death in mouse models of retinitis pigmentosa," Proceedings of National Academy of Science (U.S.A.); vol. 91:974-978, Feb. 1994.

Buchi, Ernst R., "Cell death in the rat retina after a pressure-induced ischaemia-reperfusion insult: An electron microscopic study. I. Ganglion cell layer and inner nuclear layer," Experience Eye Research. vol. 55:605-613. 1992.

Quigley, et al., "Retinal ganglion cell death in experimental glaucoma and after axotomy occurs by apoptosis," Investigative Ophthalmology & Visual Science, vol. 36(5):774-786, Apr. 1995.

Zigman, et al., "The response of mouse ocular tissues to continuous near-UV light exposure," Investigative Ophthalmology & Visual Science, vol. 14(9):710-713, Sep. 1975.

Kuwahara, et al., "Retinal damage by visible light," Archives of Ophthalmology, vol. 79:69-78, 1968.

LaVail, Matthew M., "Survival of some photoreceptor cells in ablino rats following long-term exposure to continuous light," Investigative Ophthalmology & Visual Science, vol. 15(1):64-70, Jan. 1976.

Lawwill, Theodore, "Effects of prolonged exposure of rabbit retina to low-intensity light," Investigative Ophthalmology & Visual Science, vol. 12(1):45-51, Jan. 1973.

Collier, et al., "Comparison of retinal photochemical lesions after exposure to near-uv or short-wavelength visible radiation," Inherited and Environmentally Induced Retinal Degenerations, Alan R. Liss, Inc., New York, pp. 569-575.

Collier, et al., "Temporal sequence of changes to the gray squirrel retina after near-uv exposure," Investigative Ophthalmology & Visual Science, vol. 30(4):631-637, Apr. 1989.

Tso, M.O.M., "Photic maculopathy in rhesus monkey," Investigative Ophthalmology & Visual Science, vol. 12(1):17-34; Jan. 1973.

Ham, et al., "The nature of retinal radiation damage: Dependence on wavelength, power level and exposure time," Vision Research, vol. 20:1105-1111, 1980.

Sperling, et al., "Differential spectral photic damage to primate cones," Vision Research, vol. 20:1117-1125; 1980.

Sykes, et al., "Damage to the monkey retina by broad-spectrum fluorescent light," Investigative Ophthalmology & Visual Science, vol. 20(4);425-433, Apr. 1981.

Lawwill, Theodore, "Three major pahtologic processes caused by light in the primate retina: a search for mechanisms," Transactions of the American Ophthalmology Society, vol. 80:517-579, 1982.

Marshall, et al., "Histopathology of ruby and argon laser lesions in monkey and human retina," British Journal of Ophthalmology, vol. 59:610-630, 1975.

Green, et al., "Pathologic findings of photic retinopathy in the human eye," American Journal of Ophthalmology, vol. 112:520-527, Nov. 1991.

Cruickshanks, et al., "Sunlight and age-related macular degeneration the beaver dam eye study," Archives of Ophthalmology, vol. 111:514-518, Apr. 1993.

Cayouette, et al., "Intraocular gene transfer of ciliary neurotrophic factor prevents death and increases responsiveness of rod photoreceptors in the retinal degeneration slow mouse," The Journal of Neuroscience. vol. 18(22)9282-9293. Nov. 1998.

Cayouette, et al., "Adenovirus-mediated gene transfer of ciliary neurotrophic factor can prevent photoreceptor degeneration in the retinal degeneration (rd) mouse," Human Gene Therapy, vol. 8:423-430, Mar. 1997.

\* Significantly different than vehicle (p<0.05).

\*\* Significantly different than vehicle (p<0.05) and not different than control.

* Significantly better retinal responses compared to vehicle dosed rats ($p<0.05$).

* Significantly better retinal responses compared to vehicle dosed rats (p<0.05).

USE OF β-ADRENOCEPTOR ANTAGONISTS FOR THE MANUFACTURE OF A MEDICAMENT FOR THE TREATMENT OF DISORDERS OF THE OUTER RETINA

This application claims priority from PCT/US00/32575 filed on Nov. 29, 2000, and U.S. Ser. No. 60/167,993, filed on Nov. 30, 1999.

This invention is directed to the use of β-adrenoceptor antagonists, such as, betaxolol, for treating disorders of the outer retina.

BACKGROUND OF THE INVENTION

To date, more than 100 genes have been mapped or cloned that may be associated with retinal degeneration. The pathogenesis of retinal degenerative diseases such as age-related macular degeneration (ARMD) and retinitis pigmentosa (RP) is multifaceted and can be triggered by environmental factors in those who are genetically predisposed. One such environmental factor, light exposure, has been identified as a contributing factor to the progression of retinal degenerative disorders such as ARMD (Young, *Survey of Ophthalmology*, 1988, Vol. 32:252–269). Photo-oxidative stress leading to light damage to retinal cells has been shown to be a useful model for studying retinal degenerative diseases for the following reasons: damage is primarily to the photoreceptors and retinal pigment epithelium (RPE) of the outer retina (Noell, et al., *Investigative Ophthalmology & Visual Science*, 1966, Vol. 5:450–472; Bressler, et al., *Survey of Ophthalmology*, 1988, Vol. 32:375–413; Curcio, et al., *Investigative Ophthalmology & Visual Science*, 1996, Vol. 37:1236–1249); they share a common mechanism of cell death, apoptosis (Ge-Zhi, et al., *Transactions of the American Ophthalmology Society*, 1996, Vol. 94:411–430; Abler, et al., *Research Communications in Molecular Pathology and Pharmacology*, 1996, Vol. 92:177–189); light has been implicated as an environmental risk factor for progression of ARMD and RP (Taylor, et al., *Archives of Ophthalmology*, 1992, Vol. 110:99–104; Naash, et al., *Investigative Ophthalmology & Visual Science*, 1996, Vol. 37:775–782); and therapeutic interventions which inhibit photo-oxidative injury have also been shown to be effective in animal models of heredodegenerative retinal disease (LaVail, et al., *Proceedings of the National Academy of Science*, 1992, Vol. 89:11249–11253; Fakforovich, et al., *Nature*, 1990, Vol. 347:83–86).

A number of different classes of compounds have been reported to minimize retinal photic injury in various animal models, including: antioxidants, such as, ascorbate (Organisciak, et al., *Investigative Ophthalmology & Visual Science*, 1985, Vol. 26:1580–1588), dimethylthiourea (Organisciak, et al., *Investigative Ophthalmology & Visual Science*, 1992, Vol. 33:1599–1609; Lam, et al., *Archives of Ophthalmology*, 1990, Vol.108:1751–1757). α-tocopherol (Kozaki, et al., *Nippon Ganka Gakkai Zasshi*, 1994, Vol. 98:948–954), and β-carotene (Rapp, et al., *Current Eye Research*, 1996, Vol. 15:219–223); calcium antagonists, such as, flunarizine, (Li, et al., *Experimental Eye Research*, 1993, Vol. 56:71–78; Edward, et al., *Archives of Ophthalmology*, 1992, Vol. 109:554–622); growth factors, such as, basic-fibroblast growth factor (bFGF), brain-derived nerve factor (BDNF), ciliary neurotrophic factor (CNTF), and interleukin-1-β (LaVail, et al., *Proceedings of the National Academy of Science*, 1992, Vol. 89: 11249–11253); glucocorticoids, such as, methylprednisolone (Lam, et al., *Graefes Archives of Clinical & Experimental Ophthalmology*, 1993, Vol. 231:729–736), dexamethasone (Fu, J., et al., *Experimental Eye Research*, 1992, Vol. 54:583–594); NMDA-antagonists, such as, eliprodil and MK-801 (Collier, et al., *Investigative Ophthalmology & Visual Science*, 1999, Vol. 40, pg. S159) and iron chelators, such as, desferrioxamine (Li, et al., *Current Eye Research*, 1991, Vol. 2:133–144).

Ophthalmic β-adrenergic antagonists, also referred to as β-adrenoceptor antagonists or β-blockers are well documented IOP-lowering agents for therapy of glaucoma. Currently, several ophthalmic β-blockers are approved for use worldwide. The majority of these are nonselective β-blockers; betaxolol is a cardioselective β-blocker marketed as Betoptic® or Betoptic®S (Alcon Laboratories, Inc., Fort Worth, Tex.).

As a potential treatment for glaucoma and other inner retina pathologies, Osborne, et al. (Brain Research, 1997, Vol. 751:113–123) have shown that betaxolol is neuroprotective in a rat ischemia/reperfusion injury model. Ischemia/reperfusion results in a reduction of the electroretinogram (ERG) b-wave amplitude, a measure of inner retina function, not photoreceptor or RPE function. This ERG b-wave deficit was protected by treatment with betaxolol. Consistent with the inner retinal protection was preservation of choline acetyltransferase and calretinin immunoreactivity in the inner plexiform layer and cell bodies in the ganglion cell layer and inner nuclear layer by treatment with betaxolol. In vitro studies by Osborne, et al. have also shown that betaxolol can prevent the kainate induced elevation of intracellular calcium in chick retinal cells, partially inhibited changes in GABA immunoreactivity in the rabbit inner retina following glucose-oxygen deprivation, and partially prevented the glutamate-induced release of lactate dehydrogenase in cortical cultures. β-adrenoceptor antagonists have also been shown to relax KCl-induced contraction of porcine ciliary artery (Hester, et al., *Survey of Ophthalmology*, Vol. 38:S125–S134, 1994). Moreover, certain β-blockers have been shown to produce vasorelaxation unrelated to their β-adrenergic blocking action (Yu, et al., *Vascular Risk Factors and Neuroprotection in Glaucoma*, pp. 123–134, (Drance, S. ed.) Update, 1996; Hoste, et al., *Current Eye Research*, Vol. 13:483–487, 1994; and Bessho, et al., *Japanese Journal of Pharmacology*, Vol.55:351–358, 1991.) There is experimental evidence that this is due to the ability of certain β-blockers to act as calcium channel blockers and to reduce the entry of calcium ion into vascular smooth muscle cells where it participates in the contraction response and reduces the diameter of the lumen of the blood vessel and decreases blood flow.

SUMMARY OF THE INVENTION

Figure 1A:
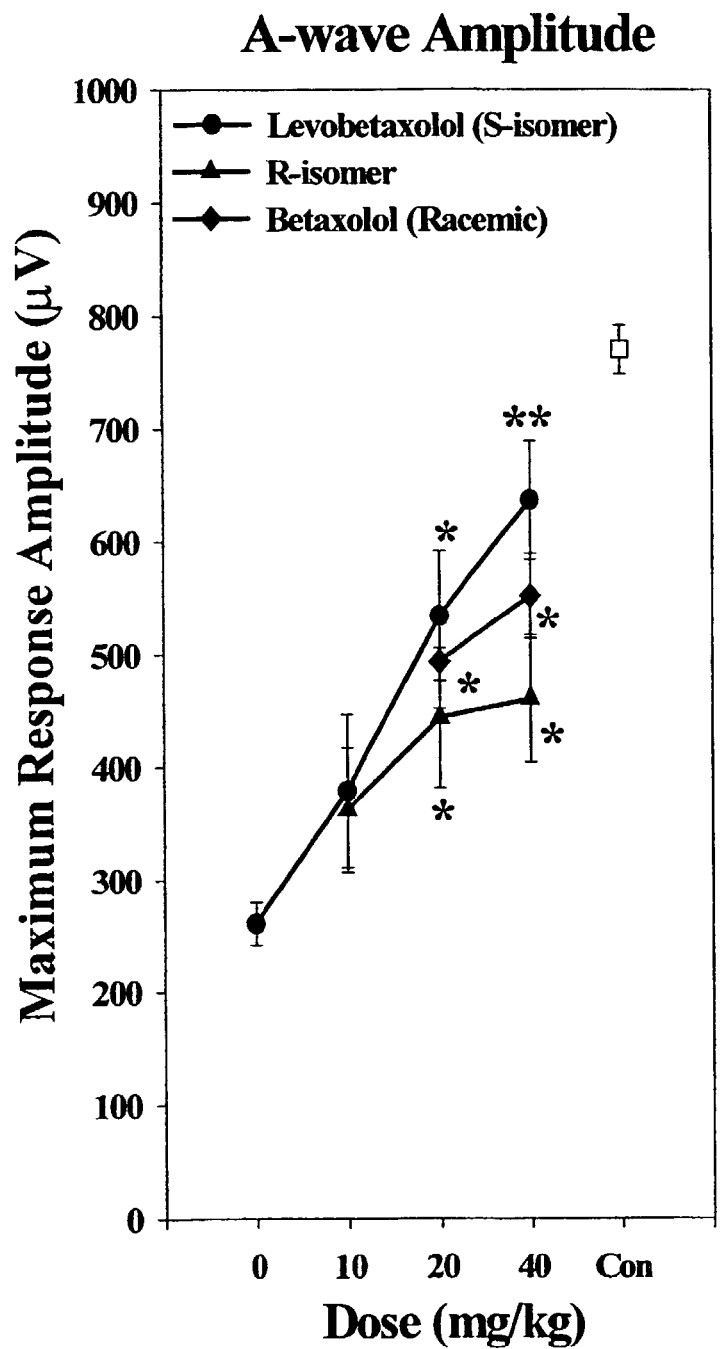
FIG. 1 shows the prevention of photic retinopathy by the systemic administration of the selective $\beta_1$-blockers, betaxolol and its isomers.

The present invention is directed to β-adrenoceptor antagonists which have been discovered to be useful in treating disorders of the outer retina, particularly: ARMD; RP and other forms of heredodegenerative retinal disease; retinal detachment and tears; macular pucker; ischemia affecting the outer retina; damage associated with laser therapy (grid, focal, and panretinal) including photodynamic therapy (PDT); trauma; surgical (retinal translocation, subretinal surgery, or vitrectomy) or light induced iatrogenic retinopathy; and preservation of retinal transplants. As used herein, the outer retina includes the RPE, photoreceptors, Muller cells (to the extent that their processes extend into the outer retina), and the outer plexiform layer. The compounds are formulated for systemic or local ocular delivery.

DETAILED DESCRIPTION OF PREFERRED EMBODIMENTS

Neurotrophic factors can be potent neuroprotective agents, but as peptides, are difficult to deliver to the retina or central nervous system. We have demonstrated that s betaxolol upregulates CNTF and bFGF MRNA retinal expression and this can prevent light-induced apoptotic cell death to the outer retina. We have found that treatment with betaxolol can completely prevent photo-oxidative induced retinopathy and significantly reduce loss of retinal function. The safety advantages of the compound make it particularly desirable for both acute and chronic therapies. Such an agent would have utility in the treatment of various outer retinal degenerative diseases.

In our light damage paradigms, antioxidants were either ineffective (alpha-tocopherol) or marginally effective at high doses (ascorbate, vitamin E analogs). Similarly, some calcium antagonists (flunarizine, nicardipine) were moderately effective while others (nifedipine, nimodipine, verapamil) had no effect in preventing light-induced functional or morphological changes. However, it has been discovered that β-adrenoceptor antagonists are effective in these light damage paradigms and therefore are useful for treating disorders of the outer retina.

Disorders of the outer retina encompass acute and chronic environmentally induced (trauma, ischemia, photo-oxidative stress) degenerative conditions of the photoreceptors and RPE cells in normal or genetically predisposed individuals. This would include, but not be limited to, ARMD, RP and other forms of heredodegenerative retinal disease, retinal detachment, tears, macular pucker, ischemia affecting the outer retina, damage associated with laser therapy (grid, focal and panretinal) including photodynamic therapy (PDT), thermal or cryotherapy, trauma, surgical (retinal translocation, subretinal surgery or vitrectomy) or light induced iatrogenic retinopathy and preservation of retinal transplants.

The invention contemplates the use of any β-adrenoceptor antagonist, including their isomers and pharmaceutically acceptable salts, for treating disorders of the outer retina. Preferred β-adrenoceptor antagonists also exhibit neurotrophic activity and may have calcium antagonist activity.

Representative β-adrenoceptor antagonists useful according to the present invention include, but are not limited to: betaxolol (R or S or racemic), timolol, carteolol, levobunolol, metipranolol, befunolol, propranolol, metoprolol, atenolol, pendolol, and pinbutolol.

The preferred β-adrenoceptor antagonist is betaxolol, and/or its R or S isomer. The S-isomer is also referred to as levobetaxolol.

In general, for degenerative diseases, the β-blockers of this invention are administered orally with daily dosage of these compounds ranging between 0.001 and 500 milligrams. The preferred total daily dose ranges between 1 and 100 milligrams. Non-oral administration, such as, intravitreal, topical ocular, transdermal patch, subdermal, parenteral, intraocular, subconjunctival, or retrobulbar injection, iontophoresis or slow release biodegradable polymers or liposomes may require an adjustment of the total daily dose necessary to provide a therapeutically effective amount of the compound. The β-blockers can also be delivered in ocular irrigating solutions used during surgery, see, for example, U.S. Pat. No. 4,443,432. This patent is herein incorporated by reference. Concentrations should range from 0.001 µM to 100 µM, preferably 0.01 µM to 5 µM.

The β-blockers can be incorporated into various types of ophthalmic formulations for topical delivery to the eye. They may be combined with ophthalmologically acceptable preservatives, surfactants, viscosity enhancers, gelling agents, penetration enhancers, buffers, sodium chloride, and water to form aqueous, sterile ophthalmic suspensions or solutions or preformed gels or gels formed in situ. Ophthalmic solution formulations may be prepared by dissolving the compound in a physiologically acceptable isotonic aqueous buffer. Further, the ophthalmic solution may include an ophthalmologically acceptable surfactant to assist in dissolving the compound. The ophthalmic solutions may contain a viscosity enhancer, such as, hydroxymethylcellulose. hydroxyethylcellulose, hydroxypropylmethylcellulose. methylcellulose, polyvinyl-pyrrolidone, or the like, to improve the retention of the formulation in the conjunctival sac. In order to prepare sterile ophthalmic ointment formulations, the active ingredient is combined with a preservative in an appropriate vehicle, such as, mineral oil, liquid lanolin, or white petrolatum. Sterile ophthalmic gel formulations may be prepared by suspending the active ingredient in a hydrophilic base prepared from the combination of, for example, carbopol-940, or the like. according to the published formulations for analogous ophthalmic preparations; preservatives and tonicity agents can be incorporated.

If dosed topically, the β-blockers are preferably formulated as topical ophthalmic suspensions or solutions, with a pH of about 4 to 8. The β-blockers will normally be contained in these formulations in an amount 0.001% to 5% by weight, but preferably in an amount of 0.01% to 2% by weight. Thus, for topical presentation, 1 to 2 drops of these formulations would be delivered to the surface of the eye 1 to 4 times per day according to the discretion of a skilled clinician.

The preferred β-blocker, betaxolol (or its R or S isomer), is orally bioavailable, demonstrates a low incidence of adverse effects upon administration, and effectively crosses the blood-brain barrier indicating that effective concentrations are expected in the target tissue, the retina. Betaxolol is described in U.S. Pat. Nos. 4,252,984 and 4,311,708, the contents of which are incorporated herein by reference.

β-adrenoceptor antagonists were evaluated in our photo-oxidative induced retinopathy paradigm, a model of retinal degenerative diseases that may have utility for identifying agents for treatment of RP and ARMD. Unexpectedly betaxolol and its enantiomers, demonstrated marked potency and efficacy as a neuroprotective agent. Both photoreceptor and RPE cells were completely protected from light-induced functional changes and morphologic lesions. Timolol was also neuroprotective, but was signifiantly less potent. Additional evaluation of levobetaxolol in a transgenic rat model that has a rhodopsin mutation, which is similar to a defect observed in some human patients with heredodegenerative disease, provided significant protection of retinal function.

EXAMPLE 1

Prevention of Photo-oxidative Induced Retinopathy by Betaxolol and its Enantiomers Photic retinopathy results from excessive excitation of the RPE and neuroretina by absorption of visible or near ultraviolet radiation. Lesion severity is dependent upon wavelength, irradiance, exposure duration, species, ocular pigmentation, and age. Damage may result from peroxidation of cellular membranes, inactivation of mitochondrial enzymes such as cytochrome oxidase, and/or increased intracellular calcium. Cellular damage resulting from photo-oxidative stress leads to cell death by apoptosis (Shahinfar, et al., 1991, *Current Eye Research*, Vol. 10:47–59; Abler, et al., 1994, *Investigative Ophthalmology & Visual Science*, Vol. 35(Suppl):1517). Oxidative stress induced apoptosis has been implicated as a cause of many ocular pathologies, including, iatrogenic retinopathy, macular degeneration, RP and other forms of heredodegenerative disease, ischemic retinopathy, retinal tears retinal detachment, glaucoma and retinal neovascularization (Chang, et al., 1995, *Archives of Ophthalmology*, Vol. 113:880–886; Portera-Cailliau, et al., 1994, *Proceedings of National Academy of Science* (U.S.A.), Vol. 91:974–978; Buchi, E. R., 1992, *Experimental Eye Research*, Vol. 55:605–613; Quigley, et al., 1995, *Investigative Ophthalmology & Visual Science*, Vol. 36:774–786). Photic induced retinal damage has been observed in mice (Zigman, et al., 1975, *Investigative Ophthalmology & Visual Science*, Vol. 14:710–713), rats (Noell, et al., 1966, *Investigative Ophthalmology and Visual Science*, Vol. 5:450–473; Kuwabara, et al., 1968, *Archives of Ophthalmology*, Vol. 79:69–78; LaVail, M. M., 1976, *Investigative Ophthalmology & Visual Science*, Vol. 15:64–70), rabbit (Lawwill, T., 1973, *Investigative Ophthalmology & Visual Science*, Vol. 12:45–51), and squirrel (Collier, et al., 1989; In LaVail et al., *Inherited and Environmentally Induced Retinal Degenerations*, Alan R. Liss, Inc., New York; Collier, et al., 1989, *Investigative Ophthalmology & Visual Science*, Vol. 30:631–637), non-human primates (Tso, M. O. M., 1973, *Investigative Ophthalmology & Visual Science*, Vol. 12:17–34; Ham, et al., 1980, *Vision Research*, Vol. 20:1105–1111; Sperling, et al., 1980, *Vision Research*, Vol. 20:1117–1125; Sykes, et al., 1981, *Investigative Ophthalmology & Visual Science*, Vol. 20:425–434; Lawwill, T., 1982, *Transactions of the American Ophthalmology Society*, Vol. 80:517–577), and man (Marshall, et al., 1975, *British Journal of Ophthalmology*, Vol. 59:610–630; Green, et al., 1991, *American Journal of Ophthalmology*, Vol. 112:520–27). In man, chronic exposure to environmental radiation has also been implicated as a risk factor for ARMD (Young, R. W., 1988, *Survey of Ophthalmology*, Vol. 32:252–269; Taylor, et al., 1992, *Archives of Ophthalmology*, Vol. 110:99–104; Cruickshank, et al., 1993, *Archives of Ophthalmology*, Vol. 111:514–518).

Systemic Dosing

The purpose of Experiment 1 was to determine if selective β-adrenoceptor antagonists, in particular betaxolol (racemic), levobetaxolol (S-isomer), and betaxolol (R-isomer) are neuroprotective and can rescue retinal cells from a photo-oxidative induced retinopathy. The purpose of Experiment 2 was to determine the dose-dependent efficacy of timolol, a potent non-selective $\beta_1$- and $\beta_2$-blocker, in this photo-oxidative stress model. Male Sprague Dawley rats were randomly assigned to drug or vehicle experimental groups. Rats received three intraperitoneal (IP) injections of either vehicle or drug at 48, 24, and 0 hours prior to a 6-hour light exposure to spectrally filtered blue light (~220 fc). Control rats were housed in their home cage under normal cyclic light exposure. Control rats were not dosed with either vehicle or drug. The ERG is a non-invasive clinical measurement of the electrical response of the eye to a flash of light. The a-wave and b-wave are two components of the ERG that are diagnostic of retinal function. The a-wave reflects outer retina function and is generated by interactions between photoreceptor and RPE while the b-wave reflects inner retina function, particularly on-bipolar cells. Although the inner retina is not significantly damaged by this light exposure, the b-wave is depressed due to the lack of photoreceptor input. Changes in the a-wave amplitude or latency are diagnostic of outer retina pathology. The ERG was recorded after a five day recovery period from dark-adapted anesthetized rats (ketamine-HCl, 75 mg/Kg; xylazine, 6 mg/Kg). The eye's electrical response to a flash of light was elicited by viewing a ganzfeld. ERGs to a series of light flashes increasing in intensity were digitized to analyze temporal characteristics of the waveform and response voltage-log intensity relationship.

Results

Experiment 1: Comparison of Betaxolol with its R and S Isomer

Figure 1B:
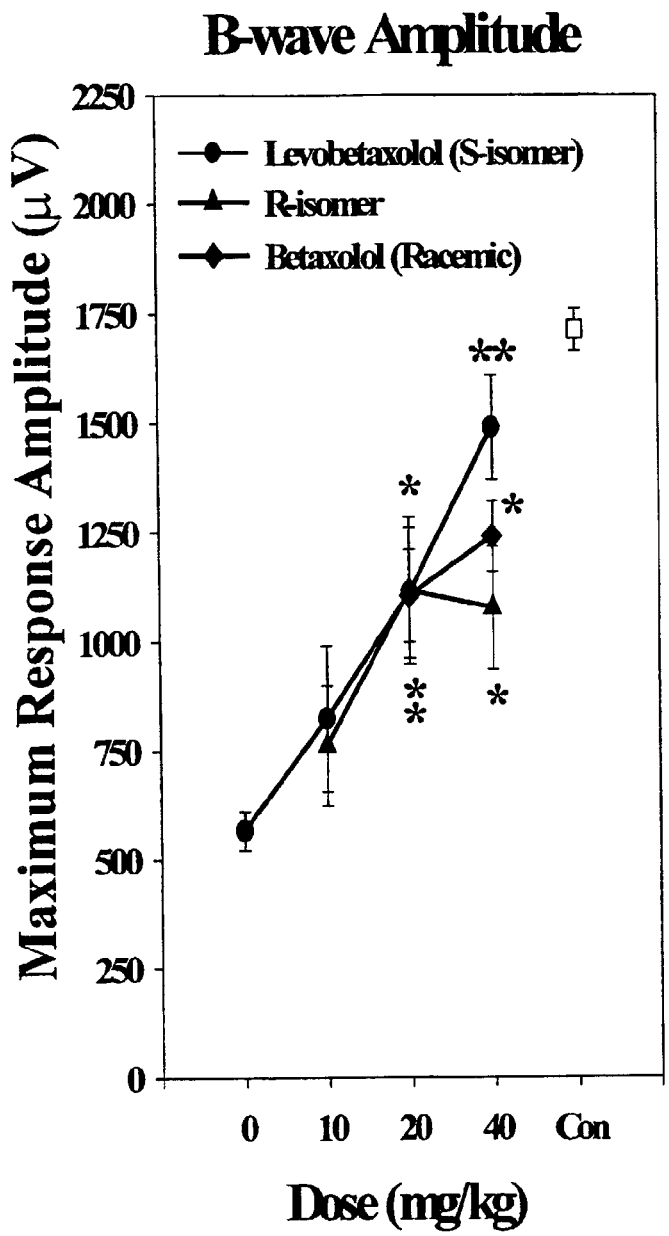

Vehicle Dosed Rats. Blue-light exposure for 6 hours resulted in a significant diminution of the ERG response amplitude (ANOVA, p<0.001) compared to controls when measured after a 5-day recovery period (FIG. 1). Maximum a-wave and b-wave amplitudes were reduced approximately 66% in vehicle-dosed rats compared to controls. In addition, threshold responses were lower and evoked at brighter flash intensities.

Betaxolol (racemic). Systemic (IP) dosing with betaxolol (racemic) provided dose-dependent protection of outer and inner retina function against this light-induced retinal degeneration in rats after a 5-day recovery period (FIG. 1). Maximum a-wave response amplitudes in betaxolol dosed rats with 20 and 40 mg/kg were 1.9 and 2.1 fold higher, respectively, than vehicle dosed rats.

Levobetaxolol (S-isomer). Systemic administration of levobetaxolol provided dose-dependent protection of outer retina function when the ERGs were measured 5 days after induction of this severe photo-oxidative induced retinopathy. Systemic dosing with 20 mg/kg and 40 mg/kg levobetaxolol afforded significant protection of retinal function to this oxidative insult (FIG. 1). ERG amplitudes in rats dosed with 20 mg/kg were 69% of normal and twice the amplitude of vehicle-dosed rats. Complete protection of the retinal response to a flash of light was measured after a 5-day recovery period in rats dosed with levobetaxolol (40 mg/kg). This protection persisted after a 4-week recovery period.

Betaxolol (R-isomer). Partial but significant protection of outer and inner retina function against light-induced retinal degeneration was measured in rats dosed with 20 and 40 mg/kg (FIG. 1). ERGs were approximately 64% of normal in rats dosed (20 or 40 mg/kg) with the R-isomer of betaxolol. This protection persisted after a 4-week recovery period.

Experiment 2: Prevention of Photic Retinopathy by Timolol

Figure 2A:
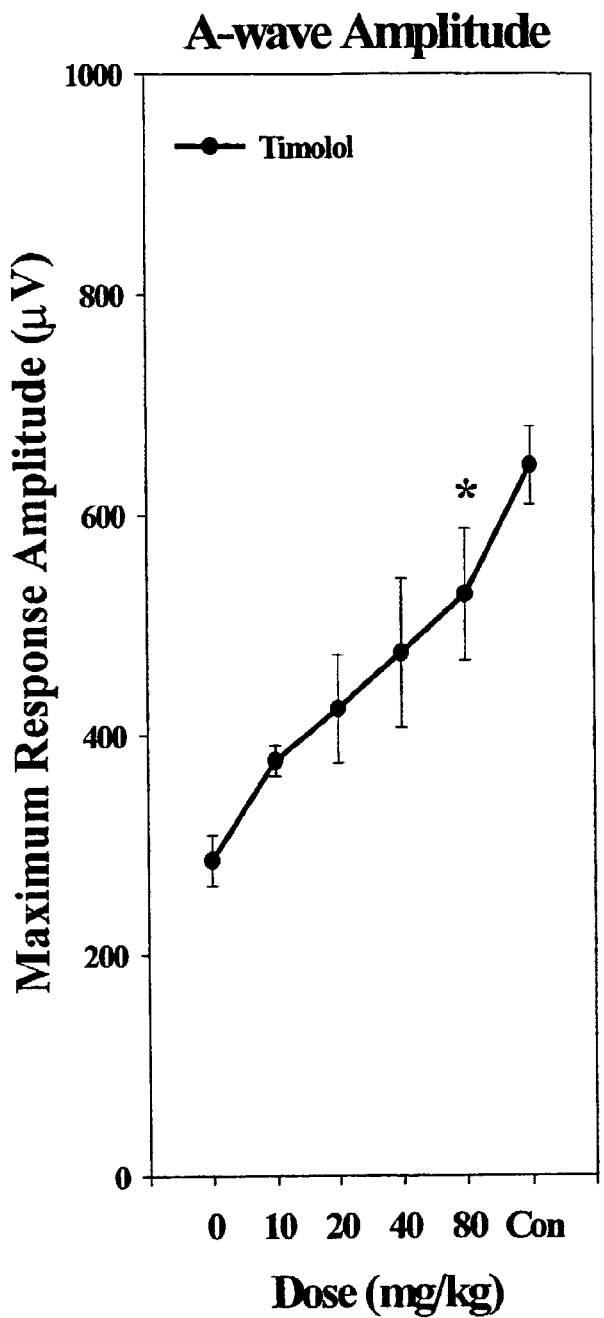
FIG. 2 shows the prevention of photic retinopathy by the systemic administration of the non-selective β-blocker, timolol.
Figure 2B:
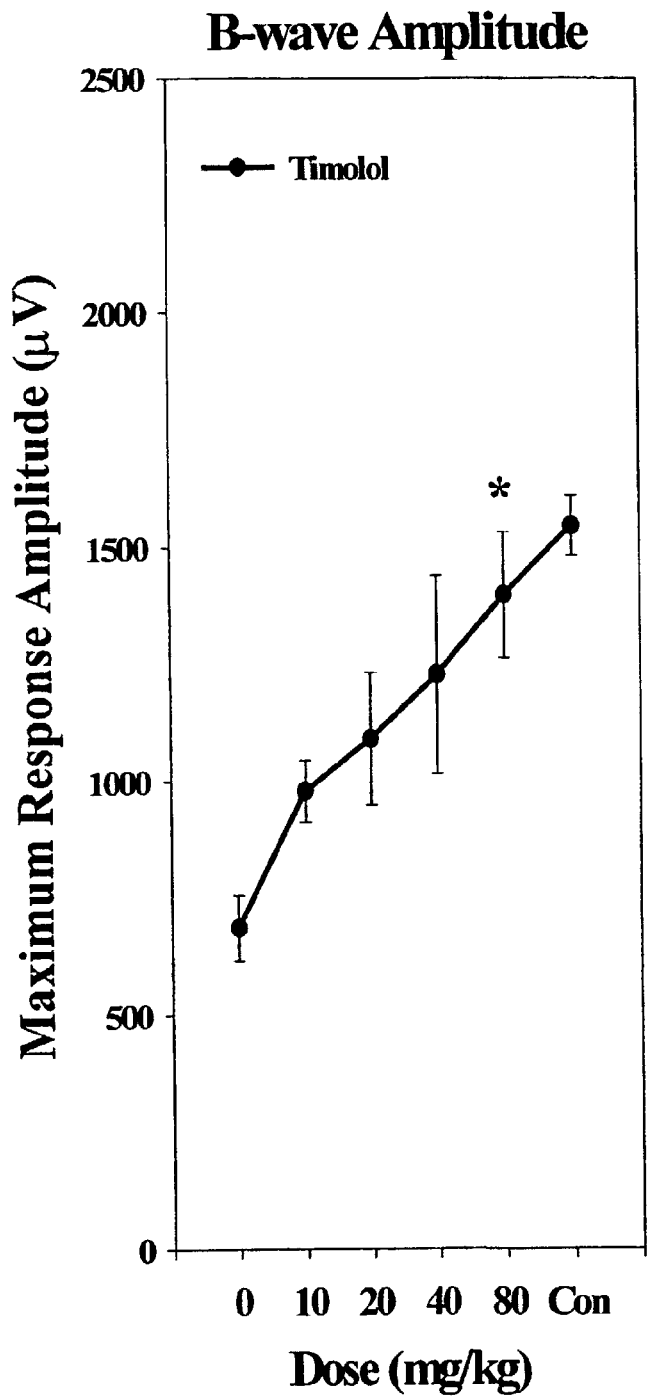

Five days after blue-light exposure, outer retinal function in vehicle dosed rats was reduced by 54% and inner retina function was reduced 52% (FIG. 2). Systemic administration (IP) of tirnolol at 10, 20, and 40 mg/kg afforded no significant protection of retinal function to this photo-oxidative insult (FIG. 2). ERGs recorded from rats dosed with 80 mg/kg were significantly better than responses measured in vehicle dosed rats.

Conclusion

Systemic administration of the β-adrenoceptor antagonists, betaxolol and its enantiomers, provided dose-dependent neuroprotection of outer and inner retina function when measured 5-days or 4-weeks after induction of a severe photo-oxidative induced retinopathy. Significant retinal protection was measured in rats dosed with these β-adrenoceptor antagonists at 20 and 40 mg/kg. This photic-induced retinopathy was prevented in rats dosed with levobetaxolol. Timolol, a non-selective β-blocker, was also effective in reducing the severity of oxidative damage to the retina as a result of this light exposure.

EXAMPLE 2

Prevention of Photo-oxidative Induced Retinopathy by Topical Ocular Dosing with Levobetaxolol The purpose of this experiment was to determine the degree of retinal protection that could be measured in rats following topical ocular dosing. Levobetaxolol (0.5%), (racemic) betaxolol (0.5%), and vehicle were evaluated in the photic retinopathy model. Induction of photochernical lesions and evaluation of retinal function with the ERG were performed as described in the photo-oxidative induced retinopathy paradigm used in Example 1.

Subjects and Dosing

Male Sprague Dawley rats were randomly assigned to either a vehicle dosed group (N=10), (racemic) betaxolol (0.5%) dosed group (N=10) or levobetaxolol (0.5%) dosed group (N=10). Rats were dosed topical ocular (b.i.d.) with two drops per eye. Rats were pre-dosed for 17 days prior to light exposure and dosed an additional two days after the light exposure. Control rats (N=4) were housed in their home cage under normal cyclic light exposure.

Results

Figure 3A:
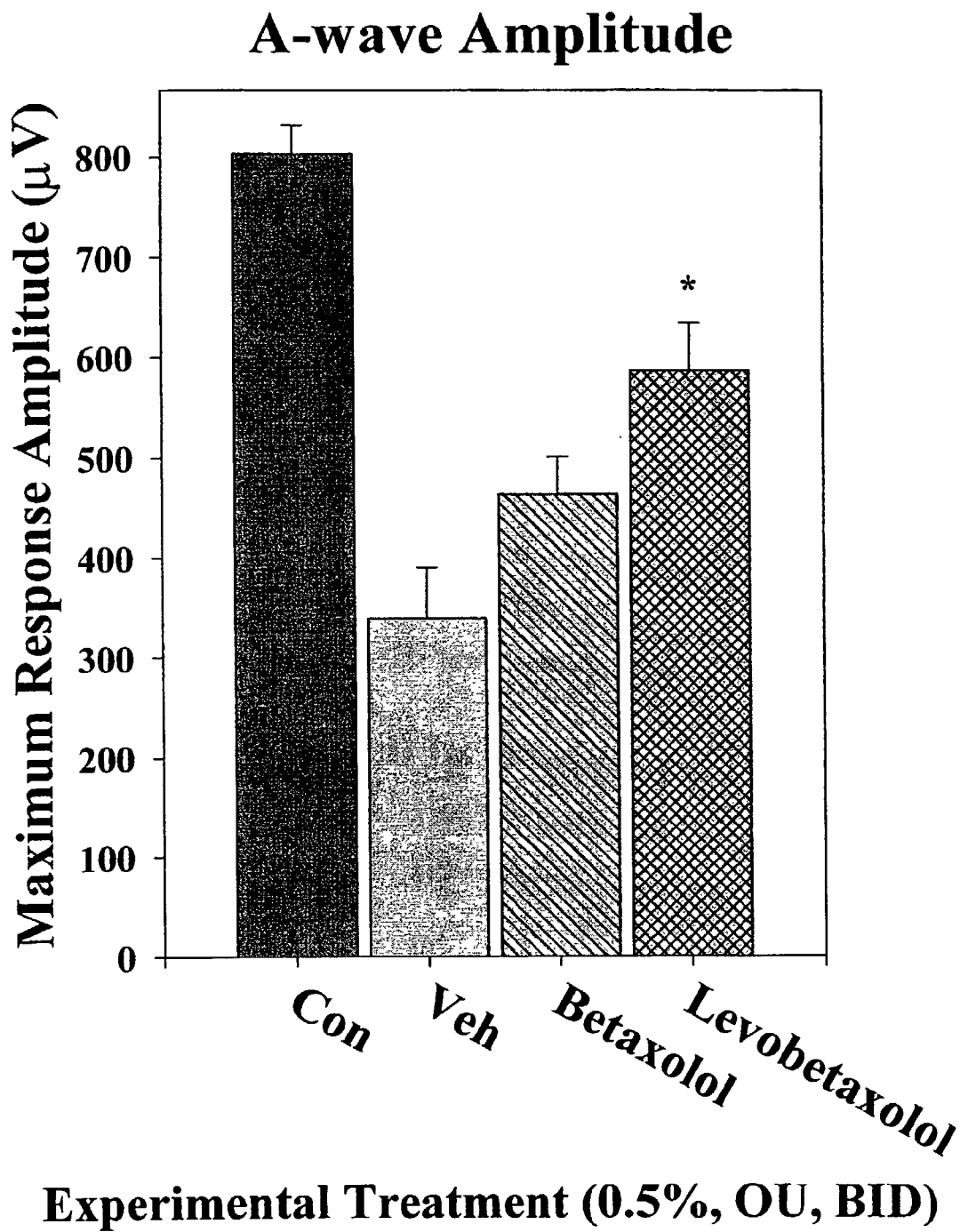
FIG. 3 compares the protection of the retina from photic retinopathy by betaxolol and levobetaxolol following topical ocular administration.
Figure 3B:
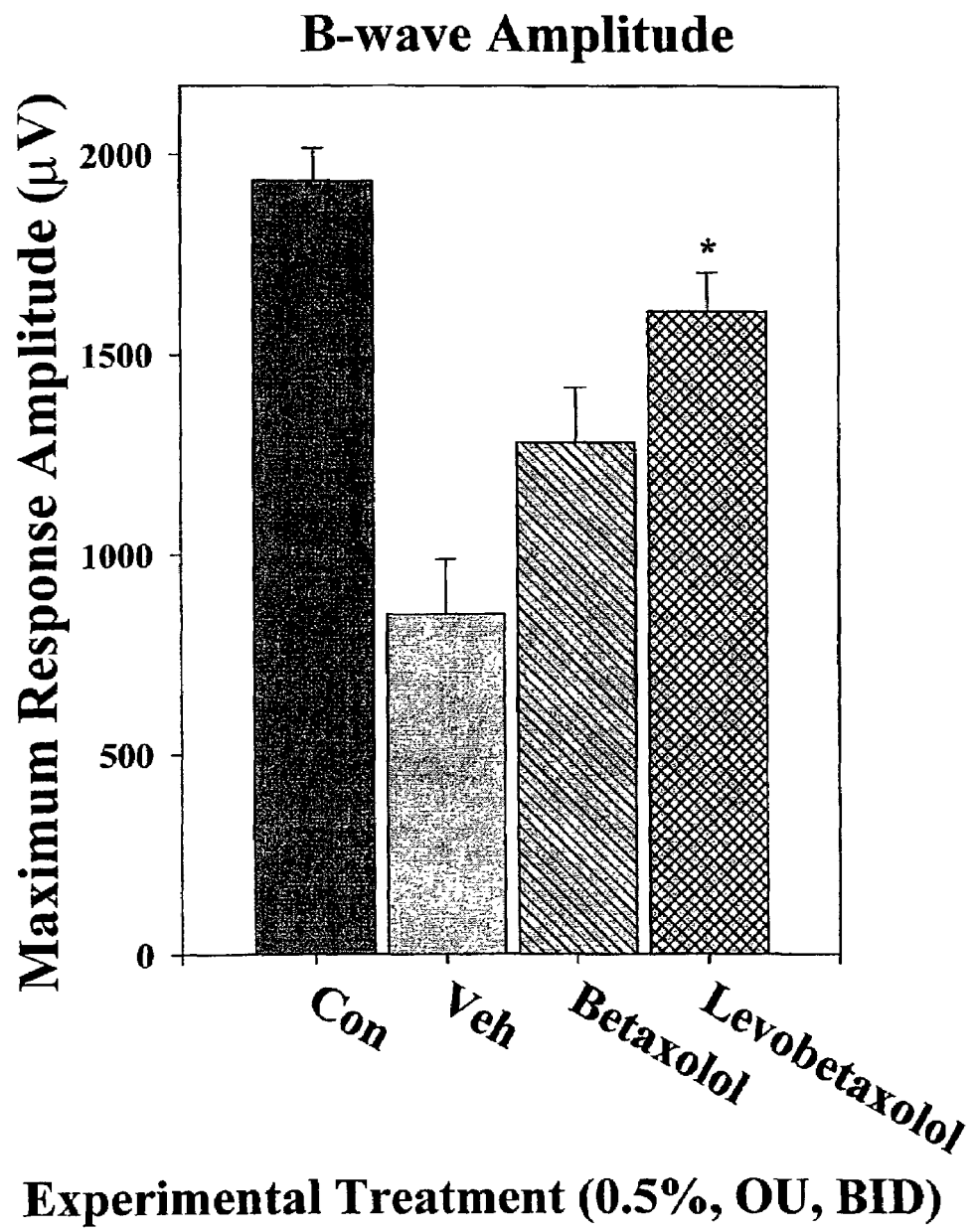

Blue-light exposure to vehicle dosed rats resulted in a significant reduction in retinal function (ANOVA, p<0.004), as measured by the electroretinogram (ERG), when measured five days after light exposure (FIG. 3). Maximum a-wave response amplitudes were reduced by 58% and inner retina function was reduced 56%.

Topical ocular dosing with levobetaxolol (b.i.d.) provided significant protection when compared to vehicle dosed rats (FIG. 3). Further, levobetaxolol completely ameliorated this photic induced retinopathy as no significant difference in retinal function was detected between control and levobetaxolol dosed rats.

No significant protection was measured in betaxolol (racemic) dosed rats. In betaxolol dosed rats, ERG response amplitudes were higher but not significantly different than responses measured from vehicle dosed rats.

EXAMPLE 3

Preservation of Visual Function in Transgenic Rats by Levobetaxolol

The P23H rhodopsin mutated transgenic rat has a specific rhodopsin mutation that has been identified in subsets of patients with RP. This degeneration is characterized by a slow degeneration of retinal photoreceptors and marked reduction in the electroretinogram. As in light damage, photoreceptor loss is primarily through an apoptotic process.

Methods

Subjects and Dosing

At the time of weaning, rats are randomly assigned to either a drug or vehicle group. Rats were dosed (oral gavage) with vehicle or levobetaxolol (40 mg/kg,) every other day. This dose was evaluated based on its ability to completely ameliorate a photic induced retinopathy. ERGs were recorded as described in Example 1.

Results

Figure 4A:
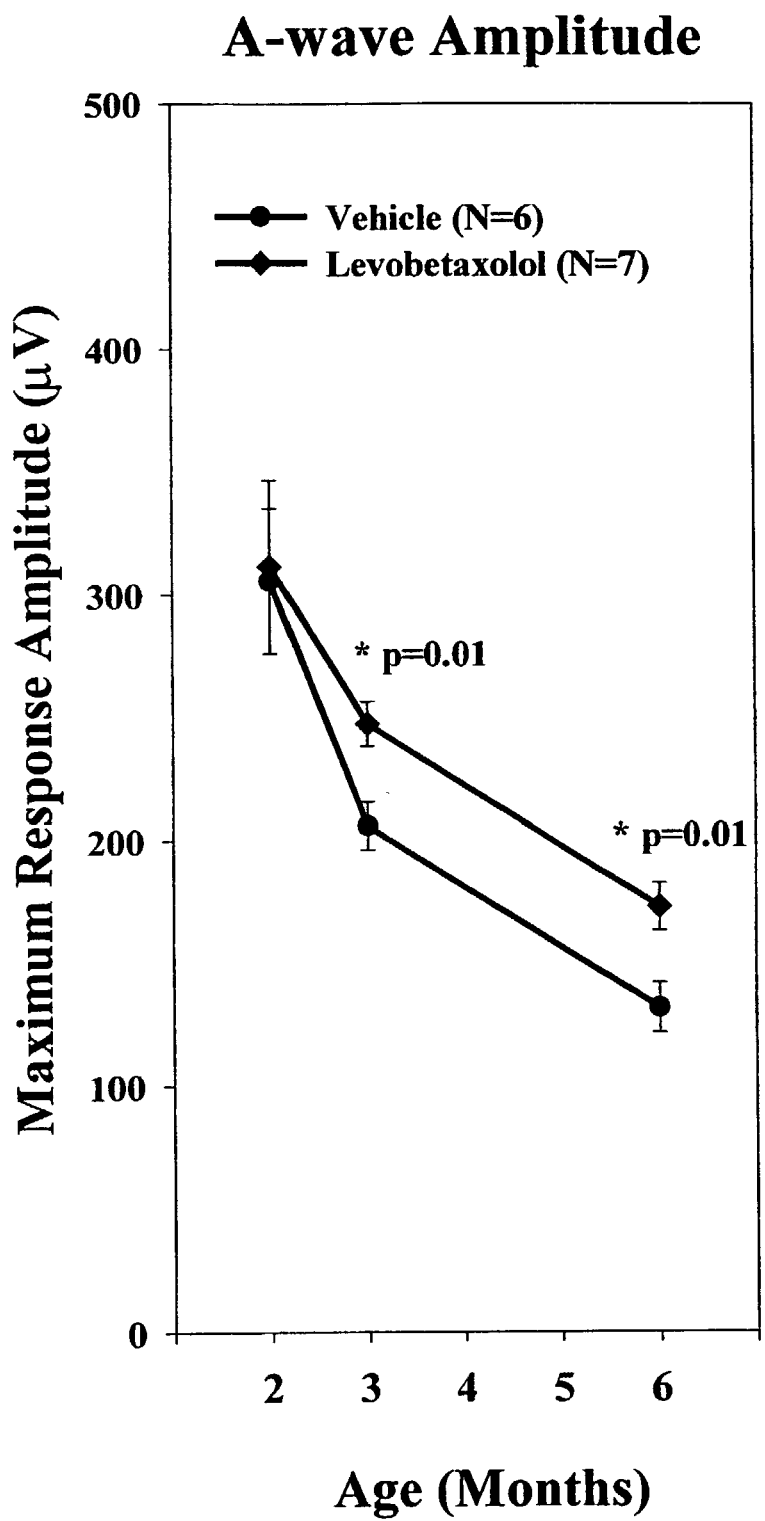
FIG. 4 shows preservation of retinal function in P23H mutant rhodopsin transgenic rats.
Figure 4B:
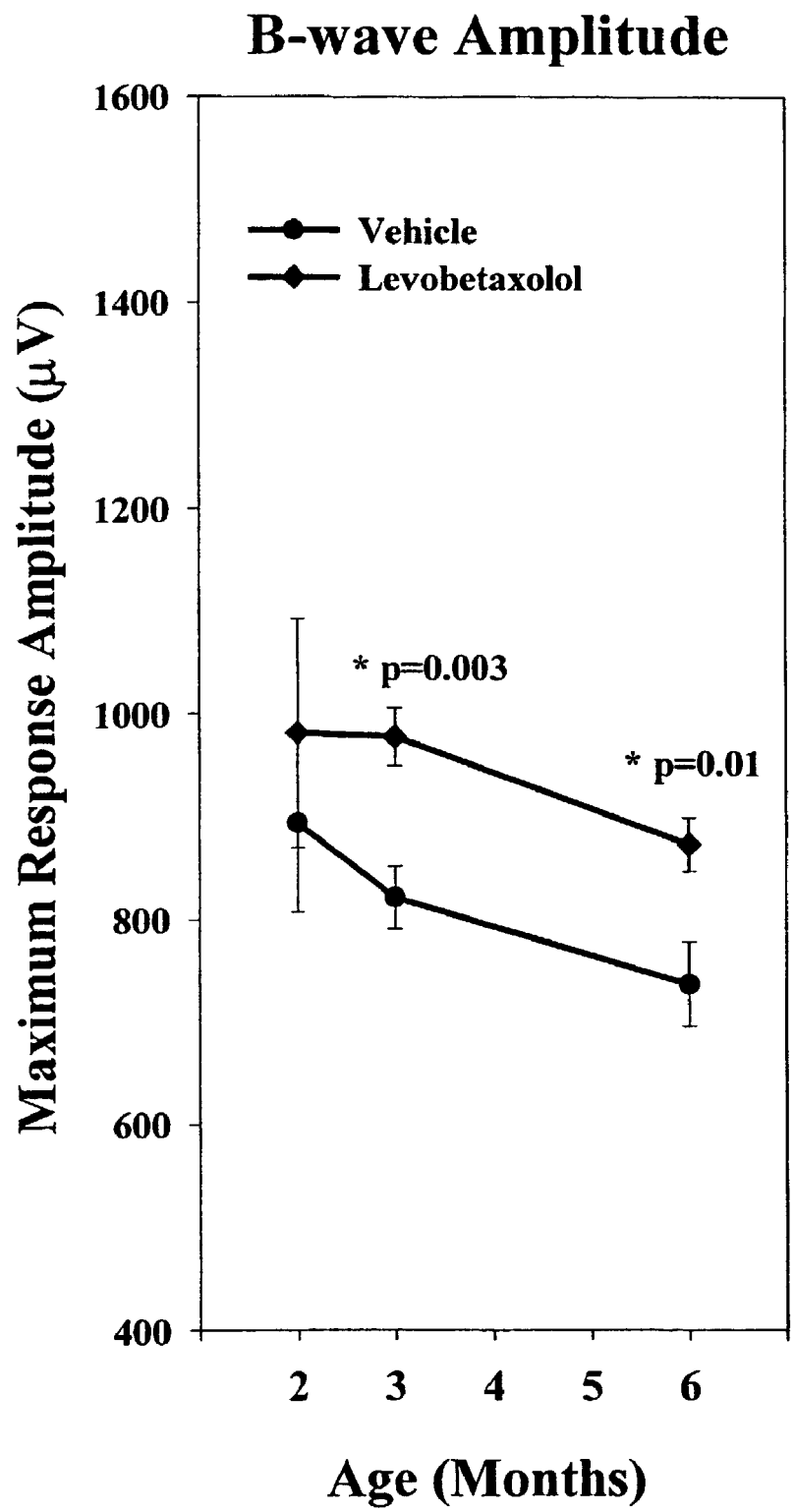

Oral dosing with levobetaxolol (40 mg/kg) every other day significantly attenuated the loss of retinal function measured in 3- and 6-month old P23H mutant rhodopsin transgenic rats compared to vehicle dosed rats (FIG. 4). Outer retinal function in 6-month old rats was 32% better than responses measured in vehicle dosed rats.

EXAMPLE 4

Upregulation of Retinal Endogenous Neurotrophic Factors by Betaxolol.

LaVail and others (Faktorovich, et al, *Nature*, Vol. 347: 83–86, 1990; LeVail, et al., Proceedings of the Naional Academy of Science, 1992, Vol. 89:11249–11253), have shown that intravitreal injection of a number of growth factors can prevent light damage to the retina. These neurotrophic factors are large peptides and don't easily cross the blood-retinal barrier. In terms of a therapeutic strategy for treatment of chronic degenerative retinal disease, repeated intravitreal injections potentially present complications, including hemorrhage, retinal detachment, and inflammation. An alternative strategy is the use of adenovirus-mediated gene transfer (bFGF in the RCS rat, Cayouette, et al, *Journal of Neuroscience*, Vol. 18(22):9282–93, 1998, and CNTF in the rd mouse, Cayouette, et al., *Human Gene Therapy*, Vol. 8(4):423–30, 1997), which has had limited success in preventing photoreceptor loss due to loss of expression over time and non-homogeneous infection of cells. We have shown that placement of genetically engineered cells into the vitreous that secrete CNTF are also effective in preventing an oxidative induced retinopathy. A recent strategy has been to identify pharmacologic agents that upregulate endogenous growth factors. Wen et al, (WO 98/10758, Mar. 19, 1998), have shown that $\alpha_2$-adrenoceptor agonists can upregulate bFGF and prevent photic injury. To determine if a β-adrenergic antagonist can induce endogenous production of neurotrophic factors, levobetaxolol was evaluated.

Evaluation of Levobetaxolol

Male albino Sprague Dawley rats were given a single IP injection of either an $\alpha_2$-adrenoceptor agonist (brimonidine) (20 mg/kg), a β-adrenergic antagonist (levobetaxolol) (20 mg/kg), or vehicle and maintained in the dark for 12 hours prior to harvesting of retinal tissue. Dark-adapted normal control rats were also evaluated. Endogenous retinal growth factor mRNA upregulation was determined by Northern blot analysis. Retinas were flash frozen in liquid nitrogen and stored until isolation of total RNA. RNA samples were run on a 1.2% agarose gel, transferred to nylon membranes, prehybridized, hybridized with labeled cDNA probes for 16 hours, washed, and exposed to X-ray film. The blots were then stripped and reprobed with an oligo specific for the 18S RNA. The bands specific for bFGF, CNTF and 18S RNA were scanned in a gel image scanner and analyzed.

RESULTS

Figure 5:
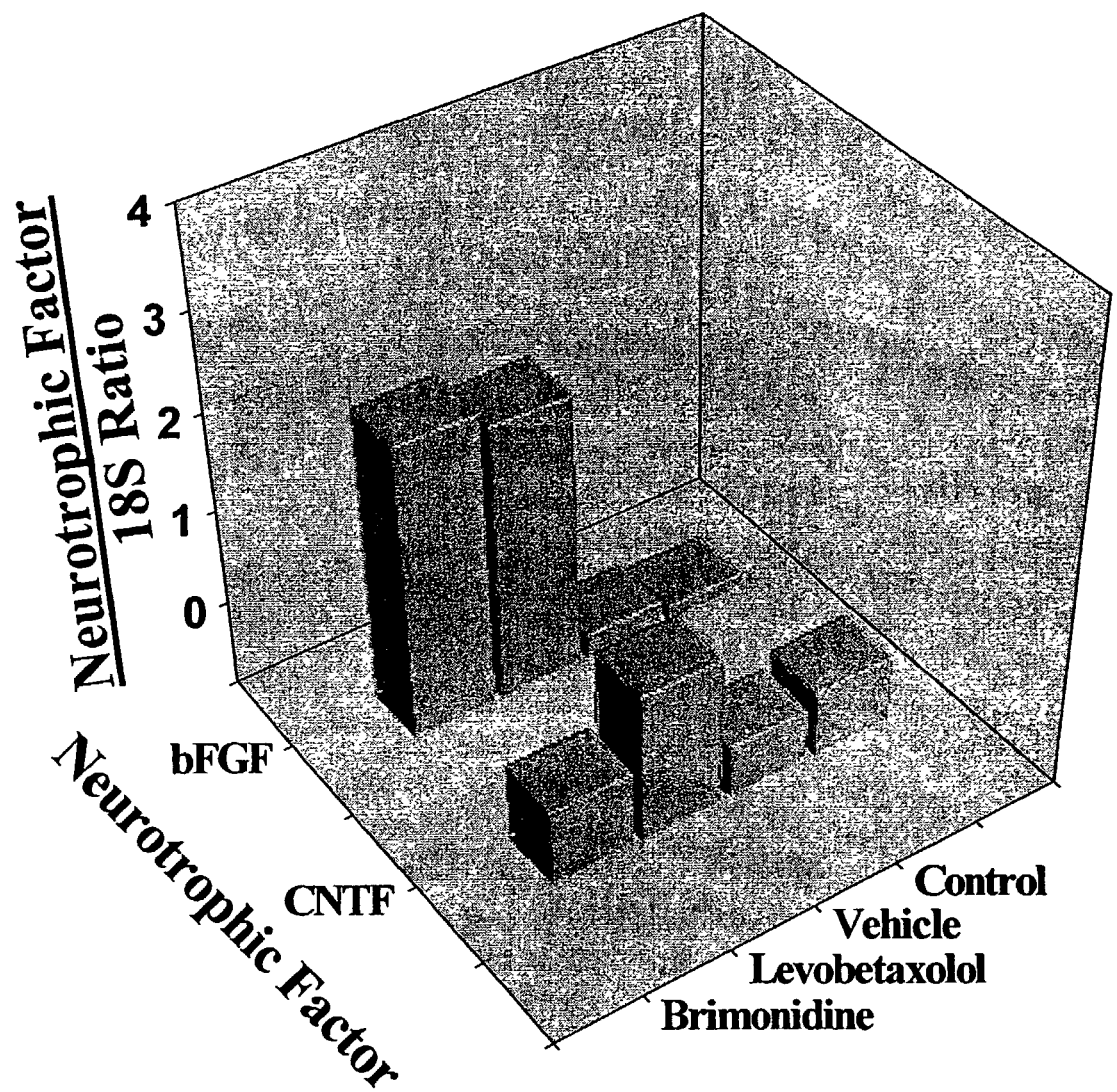
FIG. 5 shows upregulation of endogenous retinal neurotrophic factor mRNA levels following a single administration of levobetaxolol compared to other agents.

No difference was observed in the bFGF/18S or CNTF/18S ratio between vehicle dosed and control rats (FIGS. 5).

A single dose of brimonidine (20 mg/kg) resulted in a 14 fold increase in bFGF mRNA expression (FIG. 5). However, CNTF mRNA expression was not upregulated in these rats.

Similarly, levobetaxolol, a β-adrenergic antagonist, induced a 13-fold increase in bFGF mRNA expression in rats receiving a single IP injection (20 mg/kg) (FIG. 5). In addition to upregulating bFGF in these rodent retinas. endogenous CNTF mRNA expression was upregulated by a factor of 2.3 compared to background expression. Treatment with recombinant-CNTF has been shown to be efficacious in prevention of photic retinopathy and retinal heredodegenerative change.

CONCLUSION

We unexpectedly found that levobetaxolol was a potent inducer of endogenous bFGF mRNA. Unlike α-adrenoceptor agonists, levobetaxolol also resulted in a marked elevation of CNTF mRNA expression. Further, we have demonstrated that dosing with levobetaxolol, betaxolol (racemic) or its R-isomer provided significant protection to the retina when stressed with a severe photo-oxidative insult. The upregulation of CNTF mRNA is particularly important in treatment of retinopathy. The efficacy of CNTF or its analogue in preventing outer retinal degeneration has been demonstrated in the rat and mouse phototoxicity model, RCS dystrophic rat, Rdy cat suffering a rod-cone dystrophy, retinal degeneration canine model, transgenic rat (P23H and Q344ter), transgenic mouse (Q344ter), rd mouse and rds mouse. On the other hand, bFGF has only demonstrated efficacy in the rat and mouse phototoxicity model and RCS dystrophic rat.

Based on these novel findings we conclude that β-adrenoceptor antagonists, in particular levobetaxolol and betaxolol, are neuroprotective in transgenic rat and photo-oxidative stress models (FIGS. 1, 2, 3, and 4) and would be effective in the treatment of various ophthalmic degenerative diseases of the outer retina. Neuroprotection may be afforded by upregulation of endogenous neurotrophic factors. including, CNTF and bFGF (FIG. 5).

EXAMPLE 5

Levobetaxolol Hydrochloride Formulations

| Ingredient | 0.25% Percent w/v | 0.5% Percent w/v | 0.75% Percent w/v |
|---|---|---|---|
| Levobetaxolol hydrochloride | 0.28[a] | 0.56[b] | 0.84[c] |
| Poly(styrene divinylbenzene) Sulfonic Acid | 0.375 | 0.75 | 1.125 |
| Carbomer 974 P | 0.35 | 0.35 | 0.35 |
| Mannitol | 4.5 | 4.0 | 3.67 |
| Boric Acid | 0.3 | 0.3 | 0.3 |
| Disodium Edetate | 0.01 | 0.01 | 0.01 |
| Benzalkonium Chloride | 0.01 + 5% excess[d] | 0.01 + 5% excess[d] | 0.01 + 5% excess[d] |
| N-Lauroylsarcosine | 0.03 | 0.03 | 0.03 |
| Tromethamine | pH adjust to 6.5 | pH adjust to 6.5 | pH adjust to 6.5 |

Levobetaxolol Hydrochloride Formulations

| Ingredient | 0.25% Percent w/v | 0.5% Percent w/v | 0.75% Percent w/v |
|---|---|---|---|
| Hydrochloric Acid (if needed) | 6.5 ± 0.2 | 6.5 ± 0.2 | 6.5 ± 0.2 |
| Purified Water | qs 100% | qs 100% | qs 100% |

[a]Equivalent to 0.25% betaxolol free base
[b]Equivalent to 0.5% betaxolol free base
[c]Equivalent to 0.75% betaxolol free base
[d]The 5% excess is added as an overage

EXAMPLE 6

| Ingredient | Betoptic ® S Ophthalmic Suspension, 0.25% | Betaxolol Ophthalmic Suspension |
|---|---|---|
| Racemic Betaxolol | 0.28 + 5% xs | 0.28 |
| Poly(styrene divinylbenzene Sulfonic Acid) | 0.25 | 0.25 |
| Carbomer 974P | 0.2 | 0.45 |
| Mannitol | 4.5 | 4.5 |
| Boric Acid | — | 0.4 |
| Edetate Disodium | 0.01 | 0.01 |
| Benzalkonium Chloride | 0.01 + 10% excess | 0.01 + 5% excess |
| N-Lauroylsarcosine | — | 0.03 |
| Tromethamine and, if needed, Hydrochloric Acid | Adjust pH 7.6 ± 0.2 | Adjust pH 7.0 ± 0.2 |
| Purified Water | qs 100 | qs 100 |

We claim:

1. A method for treating disorders of the outer retina in a patient in need thereof, which comprises administering a pharmaceutically effective amount of a β-adrenoceptor antagonist selected from the group consisting of: betaxolol (R or S or racemic), timolol, carteolol, levobunolol, metipranolol, befunolol, propranolol, metoporolol, atenolol, pendolol, and pinbutolol, wherein said disorder is selected from the group consisting of ARMD; RP; retinal detachment and tears; macular pucker; ischemia affecting the outer retina; damage associated with laser therapy (grid, focal and panretinal) including photodynamic therapy, thermal or cryotherapy; damage resulting from trauma to the eye; surgical (retinal translocation, subretinal surgery or vitrectomy) or light-induced iatrogenic retinopathy; and preservation of retinal transplant.

2. The method of claim 1 wherein the β-adrenoceptor antagonist is betaxolol or its R or S isomer.

* * * * *